United States Patent

Tanii et al.

[11] Patent Number: 5,972,312
[45] Date of Patent: Oct. 26, 1999

[54] ORAL COMPOSITION

[75] Inventors: Sayuri Tanii; Tomoko Ito, both of Osaka, Japan

[73] Assignee: Sunstar Inc., Osaka, Japan

[21] Appl. No.: 09/037,868

[22] Filed: Mar. 11, 1998

[30] Foreign Application Priority Data

Mar. 11, 1997 [JP] Japan ..................... 9-076460

[51] Int. Cl.⁶ .............. A61K 7/16; A61K 7/22; A61K 47/38

[52] U.S. Cl. .............. 424/54; 424/49; 514/781

[58] Field of Search ......................... 424/49–58

[56] References Cited

U.S. PATENT DOCUMENTS

| | | | |
|---|---|---|---|
| 5,032,387 | 7/1991 | Hill et al. | 424/49 |
| 5,178,869 | 1/1993 | Ebine et al. | 424/401 |
| 5,275,803 | 1/1994 | Dawson | 424/52 |
| 5,310,543 | 5/1994 | Dawson | 424/49 |
| 5,328,682 | 7/1994 | Pullen et al. | 424/49 |
| 5,425,953 | 6/1995 | Sintov et al. | 424/404 |
| 5,447,930 | 9/1995 | Nayak | 514/239.2 |
| 5,453,435 | 9/1995 | Raheja et al. | 514/402 |
| 5,556,848 | 9/1996 | Kimura et al. | 514/179 |
| 5,661,170 | 8/1997 | Chodosh | 514/390 |
| 5,695,746 | 12/1997 | Garlick, Jr. et al. | 424/49 |

FOREIGN PATENT DOCUMENTS

| | | | |
|---|---|---|---|
| 0 368 130 | 5/1990 | European Pat. Off. | A61K 7/16 |
| 0 422 803 A2 | 4/1991 | European Pat. Off. | A61K 7/16 |
| 0 679 390 A2 | 11/1995 | European Pat. Off. | A61K 9/12 |

*Primary Examiner*—Shep K. Rose
*Attorney, Agent, or Firm*—Sughrue, Mion, Zinn, Macpeak & Seas, PLLC

[57] ABSTRACT

A liquid oral composition is disclosed which contains a cationic bactericide as the active ingredient and a hydroxypropyl methyl cellulose. The composition has satisfactory long-term stability and can be ejected from a container and easily applied to oral tissues. It can be kept adherent especially to the surfaces of teeth for a certain period.

10 Claims, No Drawings

ORAL COMPOSITION

FIELD OF THE INVENTION

The present invention relates to a composition for oral cavity (hereinafter sometimes simply referred to as "oral composition") which contains a cationic bactericide as the active ingredient. The oral composition of the present invention is liquid, can be satisfactorily ejected from a container, is excellent in adhesion to wet surfaces such as oral tissues and in spreadability, has satisfactory long-term stability, and is useful for the treatment and prevention of oral diseases such as periodontitis, tooth decay, and halitosis.

BACKGROUND OF THE INVENTION

Cationic bactericides have potent bacteriostatic ability and high plaque formation inhibitory activity because of their excellent adsorbability onto tissues, and are hence useful for the treatment and prevention of oral diseases such as periodontitis, tooth decay, and halitosis. However, because of their cationic nature, cationic bactericides when used in combination with anionic ingredients, e.g., anionic thickeners or surfactants, may react with the anionic ingredients to lose their bactericidal activity. In order to avoid this inactivation of cationic bactericides, oral compositions employing a combination of a cationic bactericide and a nonionic thickener were proposed (see, JP-A-2-223511 (corresponding to EP 0 368 130) and JP-A-3-127718 (corresponding to EP 0 422 803)). (The term "JP-A" as used herein means an "unexamined published Japanese patent application".) However, since the compositions disclosed in these references are ordinary dentifrices and are mostly rinsed away by mouth washing after use, the pharmaceutical preparation not remaining adsorbed on oral tissues is removed.

For improving the effectiveness of such a drug, measures in enhancing the adhesive properties of a preparation itself were proposed. A generally employed technique for improving the adhesion of a preparation to wet surfaces, e.g., the mucous membrane in the oral cavity, is to incorporate a carboxyvinyl polymer, polyacrylic acid, or an analogue thereof, which each shows excellent adhesion to the mucous membrane in the oral cavity. Examples of such preparations include solid preparations for oral use and the high-viscosity gel containing a carboxyvinyl polymer and a hydroxypropyl methyl cellulose in combination as proposed by the present inventors (see JP-A-7-267839). However, these conventional preparations still have the problem that the cationic bactericide may lose its bactericidal activity when used in combination with an anionic ingredient, e.g., a carboxyvinyl polymer. Furthermore, solid preparations and high-viscosity gels have poor spreadability and are less apt to evenly spread over the whole surfaces of the oral cavity.

On the other hand, liquid oral compositions proposed so far include an aqueous gel for oral cavity containing a hydroxypropyl methyl cellulose, in which hydroxyl groups have been converted to hydrophobic groups, and having high thixotropic properties (see JP-A-6-100424) and a liquid dentifrice containing an abrasive material and hence having enhanced long-term stability (see JP-A-4-210908). Furthermore, sprayable compositions where gel-forming cellulosic polymer was compounded therein were proposed (see EP 0 679 390). However, no oral composition has been suggested which contains a cationic bactericide as the active ingredient and is satisfactory in stability, ease of administration, and adhesive property.

SUMMARY OF THE INVENTION

An object of the present invention is to provide an oral composition which contains a cationic bactericide as the active ingredient and can be ejected from a container and easily applied to oral tissues (tissues in the oral cavity).

Another object of the present invention is provide a liquid oral composition which has satisfactory long-term stability and sufficient spreadability and remains adherent to wet surfaces in the oral cavity, in particular to tooth surfaces, for a certain period of time to thereby enable the active ingredient to produce its effect continuously.

The present inventors made intensive studies in order to eliminate the problems described above. As a result, they have found that when a specific hydroxypropyl methyl cellulose is incorporated as a thickener into a liquid oral preparation containing a cationic bactericide as the active ingredient, an oral composition is obtained which can be satisfactorily ejected from a container, well adheres to oral tissues, especially to the surfaces of teeth, and is sufficiently stable as a preparation. The present invention has been completed based on this finding.

The present invention provides a liquid oral composition which contains a cationic bactericide and a hydroxypropyl methyl cellulose. The liquid oral composition of the present invention means a liquidity or viscous liquid oral composition. In the oral composition of the present invention, the hydroxypropyl methyl cellulose is contained preferably in an amount of from 0.5 to 5% by weight based on the amount of the whole composition. The hydroxypropyl methyl cellulose preferably has a degree of methoxyl group-substitution of 1.4 to 1.9. The degree of methoxyl group-subsititution is defined by an average number of hydroxyl group substituted by methoxyl group per a glucose ring unit of cellulose. The hydroxypropyl methyl cellulose preferably has a substitution mole number of hydroxypropoxyl group of from 0.15 to 0.25, more preferably from 0.20 to 0.25. The substitution mole number of hydroxypropoxyl group is defined by an average mole number of hydroxypropoxyl group added per a glucose ring unit of cellulose. The hydroxypropyl methyl cellulose preferably has from 19.0 to 24.0% by weight methoxyl groups and from 4.0 to 12.0% by weight hydroxypropoxyl groups. Furthermore, the composition is preferably a nonalcoholic preparation not containing ethanol. The oral composition of the present invention shows sufficient properties with respect to adhesion and local detention when applied to wet surfaces, and is not stimulative during use because it contains no coarse solid particles.

DETAILED DESCRIPTION OF THE INVENTION

The present invention is explained below in more detail. The liquid oral composition of the present invention is preferably a composition having a viscosity of from 20 to 200 cP. If the viscosity thereof is higher than the upper limit, it tends to be difficult to directly deliver the composition from a container to oral tissues. If the viscosity thereof is lower than the lower limit, it tends to be difficult to hold the composition on an applicator such as a toothbrush.

The composition can be formulated as various preparations such as, e.g., a coating agent for application to tooth surfaces, a mouthwash, a liquid dentifrice, a coating agent for application to the oral mucous membrane, and a coating agent for application to oral soft tissues. The oral composition of the present invention does not contain any of the water-insoluble inorganic powders employed in general dentifrices (e.g., abrasive materials and silica thickeners).

(Cationic Bactericide)

A cationic bactericide is incorporated as the active ingredient in the oral composition of the present invention. Any of the conventionally known cationic bactericides may be used in the composition. Examples thereof include quaternary ammonium salts and bis-biguanide bactericides.

Examples of the quaternary ammonium salts include decalinium chloride, benzalkonium chloride, benzethonium chloride, cetylpyridinium chloride, dodecyltrimethylammonium bromide, dodecylmethyl(2-phenoxyethyl)ammonium bromide, and benzyldimethylstearylammonium chloride. Especially preferred are cetylpyridinium chloride, benzalkonium chloride, and benzethonium chloride.

Examples of the bis-biguanide bactericides include bis-biguanidohexanes, bis-biguanide propyl ethers, bis-biguanidoxylenes, bis-biguanidodecanes, bis-biguanidododecanes, and salts thereof. Especially preferred are bis-biguanidohexanes such as chlorhexydine hydrochloride and chlorhexydine gluconate.

These cationic bactericides may be used alone or in combination of two or more thereof. The incorporation amount of the cationic bactericide is generally from 0.001 to 5.0% by weight, preferably from 0.01 to 1.0% by weight, based on the total amount of the composition. If the incorporation amount thereof exceeds the upper limit, the composition may cause tooth discoloration or has a bitter taste. On the other hand, if the amount thereof is smaller than the lower limit, a satisfactory bactericidal effect may not be obtained.

(Hydroxypropyl Methyl Cellulose)

A hydroxypropyl methyl cellulose is incorporated as a thickener in the oral composition of the present invention. A hydroxypropyl methyl cellulose is a mixed ether of cellulose with methyl and hydroxypropyl. The hydroxypropyl methyl cellulose preferably has a degree of methoxyl group-substitution of from 1.4 to 1.9. The degree of methoxyl group-subsititution is defined by an average number of hydroxyl group substituted by methoxyl group per a glucose ring unit of cellulose. The hydroxypropyl methyl cellulose preferably has a substitution mole number of hydroxypropoxyl group of from 0.15 to 0.25, more preferably from 0.20 to 0.25. The substitution mole number of hydroxypropoxyl group is defined by an average mole number of hydroxypropoxyl group added per a glucose ring unit of cellulose. The hydroxypropyl methyl cellulose for use in the present invention preferably contains from 19.0 to 24.0% by weight methoxyl groups and from 4.0 to 12.0% by weight hydroxypropoxyl groups. If the hydroxypropyl methyl cellulose has a degree of substitution outside any of the above ranges, thermal stability tends to decrease to cause phase separation.

The hydroxypropyl methyl cellulose is not particularly limited in viscosity, as long as the 2% by weight aqueous solution thereof has a viscosity of about from 10 to 100,000 cP (at 20° C.). From the standpoint of achieving the desired purpose using a hydroxypropyl methyl cellulose in a smaller addition amount, the viscosity of the 2% aqueous solution thereof is preferably about from 1,000 to 15,000 cP, more preferably from 2,000 to 10,000, furthermore preferably from 3,000 to 6,000 cP.

The incorporation amount of the hydroxypropyl methyl cellulose is generally from 0.5 to 5% by weight, preferably from 1 to 2% by weight, based on the total amount of the oral composition. If the incorporation amount of the hydroxypropyl methyl cellulose is smaller than 0.5% by weight, the composition tends to have reduced adhesive properties in the oral cavity. On the other hand, if the amount thereof exceeds 5% by weight, the composition tends to have too high a viscosity and may be difficult to eject from a container.

(Other Ingredients)

Thickeners capable of imparting some degree of suitability for ejection and adhesive properties without impairing the bactericidal activity of the cationic bactericide may be added to the oral composition of the present invention, besides the hydroxypropyl methyl cellulose. Examples of such optionally used thickeners include nonionic cellulose ethers.

It should be noted that use of hydroxypropyl cellulose or methyl cellulose is undesirable in that compositions containing these cellulose derivatives undergo phase separation during long-term storage in the presence of a cationic bactericide. It should further be noted that use of hydroxyethyl cellulose results in impaired adhesion to oral tissues, especially to tooth surfaces. Conventionally known ingredients such as nonionic surfactants, humectants, sweetening agents, flavoring agents, colorants, preservatives, and various medicinal ingredients may be suitably incorporated into the oral composition of the present invention according to the kind of the composition, as long as the effects of the present invention are not lessened by the addition thereof.

Examples of the nonionic surfactants include sucrose/fatty acid esters, maltose/fatty acid esters, maltitol/fatty acid esters, maltotriitol/fatty acid esters, maltotetraitol/fatty acid esters, maltopentaitol/fatty acid esters, maltohexaitol/fatty acid esters, maltoheptaitol/fatty acid esters, sorbitan/fatty acid esters, lactose/fatty acid esters, lactinose/fatty acid esters, polyoxyethylene/polyoxypropylene copolymers, polyoxyethylene alkyl ethers, polyoxyethylene/fatty acid esters, fatty acid alkanolamides, polyoxyethylene sorbitan/fatty acid esters, polyoxyethylene/hydrogenated castor oil, and polyglycerin/fatty acid esters. These surfactants may be used alone or in combination of two or more thereof. The incorporation amount of the surfactant is generally preferably up to 5% by weight, more preferably up to 2% by weight, based on the total amount of the composition.

Examples of the humectants include sorbitol, glycerin, ethylene glycol, propylene glycol, 1,3-butylene glycol, polyethylene glycol, polypropylene glycol, xylitol, maltitol, and lactitol. These humectants can be incorporated alone or in combination of two or more thereof. The incorporation amount thereof is from 5 to 70% by weight based on the amount of the whole composition.

Examples of the flavoring agents include anethole, carvone, menthol, eugenol, cineole, menthone, methyl salicylate, cinnamic aldehyde, limonene, ocimene, n-decyl alcohol, citronellol, a-terpineol, methyl acetate, citronellyl acetate, methyl eugenol, linalool, ethyl linalool, vanillin, thymol, spearmint oil, peppermint oil, lemon oil, orange oil, sage oil, rosemary oil, cinnamon oil, pimento oil, diatomaceous oil, perilla oil, wintergreen oil, clove oil, and eucalyptus oil. These flavoring agents may be incorporated alone or in combination of two or more thereof in an amount of about from 0.1 to 5% by weight based on the total amount of the composition.

Examples of the sweetening agents include sodium saccharin, potassium acesulfam, stevioside, levaudioside, neohesperidyl dihydrochalcone, glycyrrhizins, perillartine, thaumatin, aspartylphenylalanine methyl ester, p-methoxycinnamic aldehyde, and xylitol. These sweetening agents may be incorporated preferably in an amount of from 0.001 to 5.0% by weight, more preferably from 0.001 to 0.1% by weight, based on the total amount of the composition.

Examples of the medicinal ingredients which can be optionally incorporated into the oral composition of the present invention include nonionic bactericides such as triclosan, amphoteric bactericides such as dodecyldiaminoethylglycine, enzymes such as dextranase, amylase, protease, mutanase, and lysozyme, alkali metal monofluorophosphates such as sodium monofluorophosphate and potassium monofluorophosphate, fluorides such as sodium fluoride and stannous fluoride, vitamin derivatives, tranexamic acid, ∈-aminocaproic acid, chlorohydroxyaluminum allantoinate, dihydroxycholesterol, glycyrrhizin salts, glycyrrhetinic acid, glycerophosphates, chlorophyll, sodium chloride, caropeptide, and water-soluble inorganic phosphoric acid compounds. One or more of these ingredients can be incorporated. The fluoride may be used in an amount of from 50 to 15,000 ppm (as F⁻) by weight, preferably from 100 to 1,500 ppm by weight, based on the composition.

Examples of the preservatives include sodium benzoate, potassium sorbate, and p-hydroxybenzoate esters. Such preservatives may be incorporated alone or in combination of two or more thereof in an amount of from 0.01 to 1.0% by weight based on the total amount of the composition.

In conventional oral compositions, ethanol is generally useful for enhancing suitability for ejection. In the present invention, however, satisfactory suitability for ejection from a container can be obtained without using ethanol because of the incorporation of a specific hydroxypropyl methyl cellulose.

For the purpose of alleviating the stimulative properties of the oral composition, a known pH regulator may be used. Examples of the pH regulator include sodium citrate, hydrochloric acid, sodium hydroxide, triethanolamine, and triethylamine. The oral composition of the present invention preferably has a pH of 4 to 8.

(Preparation of Oral Composition)

The oral composition of the present invention may be produced by mixing the above-described ingredients in an ordinary manner. The oral composition obtained is preferably a liquid composition having a viscosity of from 20 to 200 cP. This composition can be formulated as preparations such as a coating agent for application to tooth surfaces, a mouthwash, a liquid dentifrice, a coating agent for application to the oral mucous membrane, and a coating agent for application to oral soft tissues. Unlike ordinary toothpastes, the oral composition of the present invention contains no inorganic particles and hence does not necessitate mouth rinsing after oral application.

The oral composition thus prepared is preferably packed into a container suitable for oral administration. This container may have a shape suitable for ejection and direct application to oral tissues. Specifically, it may be either a spray container of the pump dispenser type or a container of the squeeze type which ejects the contents from its tip by being pressed at the side of its body. Since the oral composition has a low viscosity, it is preferred to employ a container whose tip has a small opening diameter (3 mm or smaller).

The composition of the present invention may be directly applied to the affected part in the oral cavity at any time in a suitable manner, for example, by spraying the composition over the affected part with the above dispenser or another container. The dose of the composition may be suitably regulated according to the degree of affection, etc. The ejecting amount from the container per one push is preferably from 0.01 to 1 ml.

The present invention will be explained below in more detail by reference to Examples and Comparative Examples, but the invention should not be construed as being limited to these Examples. In the Examples, all "percents" are by weight. The compositions obtained in the Examples and Comparative Examples were evaluated in the following manners.

(Ejection Test)

Each sample was packed into a pump dispenser type container. The pump head part was pressed ten times at a constant pressure and the resultant flight distances were averaged. The suitability for ejection was evaluated based on the following criteria.

Criteria for Judgement

◎: flight distance of 30 cm or longer
○: flight distance of 20 to 30 cm, excluding 30 cm
Δ: flight distance of 10 to 20 cm, excluding 20 cm
x: flight distance smaller than 10 cm (Stringiness Test)

Each sample was packed into a pump dispenser type container. The pump head part was vertically pressed ten times at a constant pressure. The resultant stringing was examined for string length. The string length was a length from the tip to the end of the preparation flighted when the pump head was pressed. The stringiness was evaluated based on the following criteria.

Criteria for Judgement

◎: string length smaller than ⅓ of the flight distance
○: string length of ⅓ to ½, excluding ½, of the flight distance
Δ: string length of ½ to ⅔, excluding ⅔, of the flight distance
x: string length not smaller than ⅔ of the flight length (Adhesion Test)

Each sample was packed into a pump dispenser type container. The contents were jetted toward a vertical plane, and the time period through which the liquid applied to the vertical plane sagged or flowed down was measured. The adhesive properties were evaluated based on the following criteria.

Criteria for Judgement

◎: 3 minutes or longer
○: 1 to 3 minutes, excluding 3 minutes
Δ: 30 seconds to 1 minute, excluding 1 minute
x: shorter than 30 seconds (Long-term Stability Test)

Each sample was allowed to store at 55° C. for 1 month and then at room temperature for 1 day. The sample was visually examined for change in state.

(Comprehensive Evaluation)

Each sample was comprehensively evaluated according to the following criteria. The samples rated as ○ or ◎ with respect to each of suitability for ejection, adhesive properties, stringiness, and stability were regarded as acceptable (○). Among these, the samples which were excellent were indicated by ◎. The samples which were unsatisfactory (Δ or x) in at least one evaluation item were regarded as unacceptable (Δ or x).

Criteria for Judgement

◎: excellent
○: acceptable
Δ: slightly unsatisfactory in at least one item
x: unsatisfactory in at least one item

EXAMPLES 1 TO 3

According to the formulations shown in Tables 1 and 2, oral compositions were prepared in an ordinary manner. These compositions each had a viscosity of from 20 to 200 cP.

TABLE 1

| Ingredient | | | Example 1 | 2 | 3 | 4 | 5 |
|---|---|---|---|---|---|---|---|
| Hydroxypropyl methyl cellulose | | 2% viscosity, 1500 cP | 1.5 | — | — | — | — |
| • degree of methoxyl group-substitution: 1.4 | | 2% viscosity, 4000 cP | — | 1.5 | — | — | — |
| • substitution mole number of hydroxypropoxyl group: 0.20 | | 2% viscosity, 10,000 cP | — | — | 1.5 | — | — |
| Hydroxypropyl methyl cellulose<br>• degree of methoxyl group substitution: 1.9<br>• substitution mole number of hydroxypropoxyl group: 0.25 | | | — | — | — | 1.5 | — |
| Hydroxypropyl methyl cellulose<br>• degree of methoxyl group substitution: 1.8<br>• substitution mole number of hydroxypropoxyl group: 0.15 | | | — | — | — | — | 1.5 |
| Cationic bactericide: cetylpyridinium chloride | | | 0.015 | 0.015 | 0.015 | 0.015 | 0.015 |
| Glycerin | | | 15.0 | 15.0 | 15.0 | 15.0 | 15.0 |
| pH Regulator | | | appropriate amount | appropriate amount | appropriate amount | appropriate amount | appropriate amount |
| Purified water | | | remainder | remainder | remainder | remainder | remainder |
| Total | | | 100.0 | 100.0 | 100.0 | 100.0 | 100.0 |
| Suitability for ejection | | | ⊚ | ⊚ | ○ | ⊚ | ○ |
| Stringiness | | | ⊚ | ⊚ | ○ | ⊚ | ⊚ |
| Adhesive property | | | ○ | ⊚ | ⊚ | ○ | ○ |
| Long-term stability, change in state | | | no change | no change | no change | slight separation | slight separation |
| Comprehensive evaluation | | | ○ | ⊚ | ○ | ○ | ○ |

TABLE 2

| Ingredient | | Comparative Example 1 | 2 | 3 | 4 | 5 | 6 |
|---|---|---|---|---|---|---|---|
| Cellulose ether thickener | hydroxyethyl cellulose | 1.5 | — | — | — | — | — |
| | hydroxypropyl cellulose | — | 1.5 | — | — | — | — |
| | Methyl cellulose | — | — | 1.5 | — | — | — |
| Nonionic thickener | Poly(ethylene oxide) | — | — | — | 1.5 | — | — |
| | Poly(vinyl alcohol) | — | — | — | — | 1.5 | — |
| | Polyvinylpyrrolidone | — | — | — | — | — | 1.5 |
| Cationic bactericide: cetylpyridinium chloride | | 0.015 | 0.015 | 0.015 | 0.015 | 0.015 | 0.015 |
| Glycerin | | 15.0 | 15.0 | 15.0 | 15.0 | 15.0 | 15.0 |
| pH Regulator | | appropriate amount | appropriate amount | appropriate amount | appropriate amount | appropriate amount | appropriate amount |
| Purified water | | remainder | remainder | remainder | remainder | remainder | remainder |
| Total | | 100.0 | 100.0 | 100.0 | 100.0 | 100.0 | 100.0 |
| Suitability for ejection | | ⊚ | ⊚ | ○ | ⊚ | ⊚ | ⊚ |
| Stringiness | | ⊚ | ⊚ | ○ | Δ | ⊚ | ⊚ |
| Adhesive property | | ○ | ⊚ | ⊚ | ○ | X | X |
| Long-term stability, change in state | | separation | separation | separation | no change | no change | browning |
| Comprehensive evaluation | | X | X | X | Δ | X | X |

Remarks: The Hydroxypropyl methyl cellulose having a degree of methoxyl group-substitution of 1.4 and having a substitution number of hydroxypropoxyl group of 0.20 corresponds to a hydroxypropyl methyl cellulose having a methoxyl group in an amount of 19.0% to 24.0% by weight based on the cellulose of hydroxylpropyl methyl cellulose and having a hydroxypropoxyl group in an amount of 4.0% to 12.0% by weight based on the cellulose of hydroxypropyl methyl cellulose.

As apparent from Table 1, the oral compositions obtained in Examples 1 to 5 were satisfactory in suitability for ejection, adhesive property, and long-term stability due to the incorporation of a hydroxypropyl methyl cellulose. As apparent from Table 2, the oral compositions containing a nonionic polymer other than hydroxypropyl methyl celluloses were unsatisfactory in at least one of suitability for ejection, adhesive property, and long-term stability.

EXAMPLE 4

A liquid dentifrice was prepared according to the following formulation in an ordinary manner.

| Ingredient | Amount (wt %) |
|---|---|
| Cetylpyridinium chloride | 0.015 |
| Stevia extract | 0.003 |
| Glycerin | 15.0 |
| Hydroxypropyl methyl cellulose | 1.5 |
| Sodium fluoride | 0.022 |
| Sodium benzoate | 0.1 |
| Perfume | 0.2 |
| pH Regulator | appropriate amount |
| Purified water | remainder |
| Total | 100.0 |

(Hydroxypropyl methyl cellulose: the degree of methoxy group substitution, 1.4; the substitution mole number of hydroxypropoxyl group, 0.20; viscosity, 10,000 cP) The liquid dentifrice obtained was evaluated for properties by the methods described above. As a result, satisfactory results were obtained.

EXAMPLE 5

A liquid dentifrice was prepared according to the following formulation in an ordinary manner.

| Ingredient | Amount (wt %) |
|---|---|
| Cetylpyridinium chloride | 0.015 |
| Stevia extract | 0.003 |
| Glycerin | 15.0 |
| Hydroxypropyl methyl cellulose | 2.0 |
| Sodium fluoride | 0.022 |
| Sodium benzoate | 0.1 |
| Perfume | 0.2 |
| pH Regulator | appropriate amount |
| Colorant | slight amount |
| Purified water | remainder |
| Total | 100.0 |

(Hydroxypropyl methyl cellulose: the degree of methoxy group substitution, 1.4; the substitution mole number of hydroxypropoxyl group, 0.20; viscosity, 4,000 cP) The liquid dentifrice obtained was evaluated for properties by the methods described above. As a result, satisfactory results were obtained.

EXAMPLE 6

A coating agent for application to tooth surfaces was prepared according to the following formulation in an ordinary manner.

| Ingredient | Amount (wt %) |
|---|---|
| Chlorhexydine gluconate | 0.04 |
| Sodium saccharin | 0.02 |
| Glycerin | 15.0 |
| Hydroxypropyl methyl cellulose | 1.5 |
| Sodium monofluorophosphate | 0.07 |
| Perfume | 0.2 |
| pH Regulator | appropriate amount |
| Purified water | remainder |
| Total | 100.0 |

(Hydroxypropyl methyl cellulose: the degree of methoxy group substitution, 1.4; the substitution mole number of hydroxypropoxyl group, 0.20; viscosity, 10,000 cP) The coating agent for application to tooth surfaces obtained was evaluated for properties by the methods described above. As a result, satisfactory results were obtained.

EXAMPLE 7

A coating agent for application to oral soft tissues was prepared according to the following formulation in an ordinary manner.

| Ingredient | Amount (wt %) |
|---|---|
| Chlorhexydine gluconate | 0.02 |
| Stevia extract | 0.04 |
| Sorbitol | 20.0 |
| Hydroxypropyl methyl cellulose | 2.0 |
| Glycyrrhetinic acid | 0.04 |
| Sodium benzoate | 0.1 |
| Perfume | 0.2 |
| pH Regulator | appropriate amount |
| Colorant | slight amount |
| Purified water | remainder |
| Total | 100.0 |

(Hydroxypropyl methyl cellulose: the degree of methoxy group substitution, 1.4; the substitution mole number of hydroxypropoxyl group, 0.20; viscosity, 1,500 cP) The coating agent for application to oral soft tissues obtained was evaluated for properties by the methods described above. As a result, satisfactory results were obtained.

The present invention brings about the following effects. By incorporating a hydroxypropyl methyl cellulose into an oral composition which contains a cationic bactericide, an oral composition is obtained which is excellent in suitability for ejection, stringiness, adhesion to oral tissues, spreadability, and long-term stability while retaining the intact bactericidal activity. This oral composition is a liquid composition suitable for ejection from a container. The composition can further have the plaque formation inhibitory activity characteristic of cationic bactericides, and is hence useful for the treatment and prevention of oral diseases such as periodontitis, tooth decay, and halitosis.

While the invention has been described in detail and with reference to specific embodiments thereof, it will be apparent to one skilled in the art that various changes and modifications can be made therein without departing from the spirit and scope thereof.

What is claimed is:

1. A liquid oral composition which comprises a cationic bactericide and hydroxypropylmethyl cellulose packed into a container capable of ejecting or spraying in a predetermined amount, wherein the hydroxypropylmethyl cellulose has a degree of methoxyl group-substitution of from 1.4 to 1.9, said degree of methoxyl group-substitution being defined by an average number of hydroxyl group substituted by methoxyl group per glucose ring unit of cellulose, and the hydroxypropylmethyl cellulose has a substitution mole number of hydroxypropoxyl group of from 0.15 to 0.25, said substitution mole number of hydroxypropoxyl group being defined by an average mole number of hydroxypropoxyl group added per glucose ring unit of cellulose, and wherein said hydroxypropylmethyl cellulose is contained in an amount of 0.5% to 5% by weight based on the amount of the liquid oral composition.

2. The liquid oral composition as claimed in claim 1, wherein the hydroxypropyl methyl cellulose has a substitution mole number of hydroxylpropoxyl group of from 0.20 to 0.25.

3. The liquid oral composition as claimed in claim 1, wherein the hydroxypropyl methyl cellulose has a degree of methoxyl group-substitution of 1.4, and has a substitution mole number of hydroxypropoxyl group of from 0.20.

4. The liquid oral composition as claimed in claim 1, wherein the hydroxypropyl methyl cellulose has a methoxyl group in an amount of 19.0% to 24.0% by weight based on the cellulose of hydroxypropyl methyl cellulose, and has a hydroxypropoxyl group in an amount of 4.0% to 12.0% by weight based on the cellulose of hydroxypropyl methyl cellulose.

5. The liquid oral composition as claimed in claim 1, which is an ethanol-free preparation.

6. The liquid oral composition as claimed in claim 1, which further comprises a fluoride.

7. The liquid oral composition as claimed in claim 1, wherein the cationic bactericide is contained in an amount of 0.001% to 5.0% by weight based on the amount of the liquid oral composition.

8. The liquid oral composition as claimed in claim 1, which does not contain any inorganic particles.

9. The liquid oral composition as claimed in claim 1, which has a viscosity of from 20 to 200 cP.

10. A method for administering a liquid oral composition comprising:

applying said liquid oral composition onto an oral tissue, said liquid oral composition remaining adherent on said oral tissue;

wherein said liquid oral composition comprises a cationic bactericide and 0.5 to 5% by weight, based on the amount of the liquid oral composition, of a hydroxypropyl methyl cellulose, said hydroxypropyl methyl cellulose having a degree of methoxyl group-substitution of from 1.4 to 1.9, said degree of methoxyl group substitution being defined by an average number of hydroxyl groups substituted by methoxyl groups per glucose ring unit of cellulose, and the hydroxypropyl methyl cellulose having a substitution mole number of hydroxypropoxyl group of 0.15 to 0.25, said substitution mole number of hydroxypropoxyl group being defined by an average mole number of hydroxypropoxyl groups added per glucose ring unit of cellulose.

* * * * *